United States Patent [19]

Davis et al.

[11] Patent Number: 4,848,094
[45] Date of Patent: Jul. 18, 1989

[54] DROPLET FREEZING METHOD AND APPARATUS

[75] Inventors: Robert B. Davis, Nyack, N.Y.; Donald L. DeVack, Norwalk, Conn.

[73] Assignee: Union Carbide Corporation, Danbury, Conn.

[21] Appl. No.: 188,308

[22] Filed: Apr. 29, 1988

[51] Int. Cl.$^4$ .................................. F25D 17/02
[52] U.S. Cl. ................................ 62/64; 62/78; 62/51.1
[58] Field of Search .................. 62/64, 78, 514 R

[56] References Cited

U.S. PATENT DOCUMENTS

| | | | |
|---|---|---|---|
| 2,875,588 | 3/1959 | Berger | 62/64 |
| 3,210,443 | 10/1965 | Reddie et al. | 264/14 |
| 3,228,838 | 1/1966 | Rinfret et al. | 62/78 |
| 3,437,488 | 4/1969 | Humphreys | 99/3 |
| 3,551,533 | 12/1970 | Monforte et al. | 264/14 |
| 3,721,725 | 3/1973 | Briggs et al. | 264/6 |
| 3,755,530 | 8/1973 | Avila et al. | 423/22 |
| 3,932,943 | 1/1976 | Briggs et al. | 34/5 |
| 4,073,158 | 2/1978 | Guiller | 62/64 |
| 4,077,227 | 3/1978 | Larson | 62/74 |
| 4,149,837 | 4/1979 | Baker et al. | 425/10 |
| 4,380,518 | 4/1983 | Wydro, Sr. | 264/13 |
| 4,655,047 | 4/1987 | Temple et al. | 62/64 |
| 4,687,672 | 8/1987 | Vitrovsky | 426/524 |
| 4,704,873 | 10/1987 | Imaike et al. | 62/78 |
| 4,712,310 | 12/1987 | Roy | 34/5 |

Primary Examiner—Ronald C. Caposseia
Attorney, Agent, or Firm—Shirley L. Church; Stanley Ktorides

[57] ABSTRACT

The present invention relates to a method and apparatus for the generation of essentially spherical frozen droplets of a liquid biological or organic-comprising composition. The liquid composition if fed under positive pressure through a nozzle in a manner which provides a continuous stream of the liquid composition exiting the nozzle; the continuous stream travels through a gas or vapor for a distance sufficient to cause the continuous stream to break apart, forming droplets ranging in size from about 0.6 mm to about 5 mm; the liquid composition droplets are then contacted with a cryogenic liquid capable of freezing the droplets into a solid phase; the frozen droplets are concentrated into a portion of the contacting cryogenic liquid from which they are subsequently separated.

18 Claims, 2 Drawing Sheets

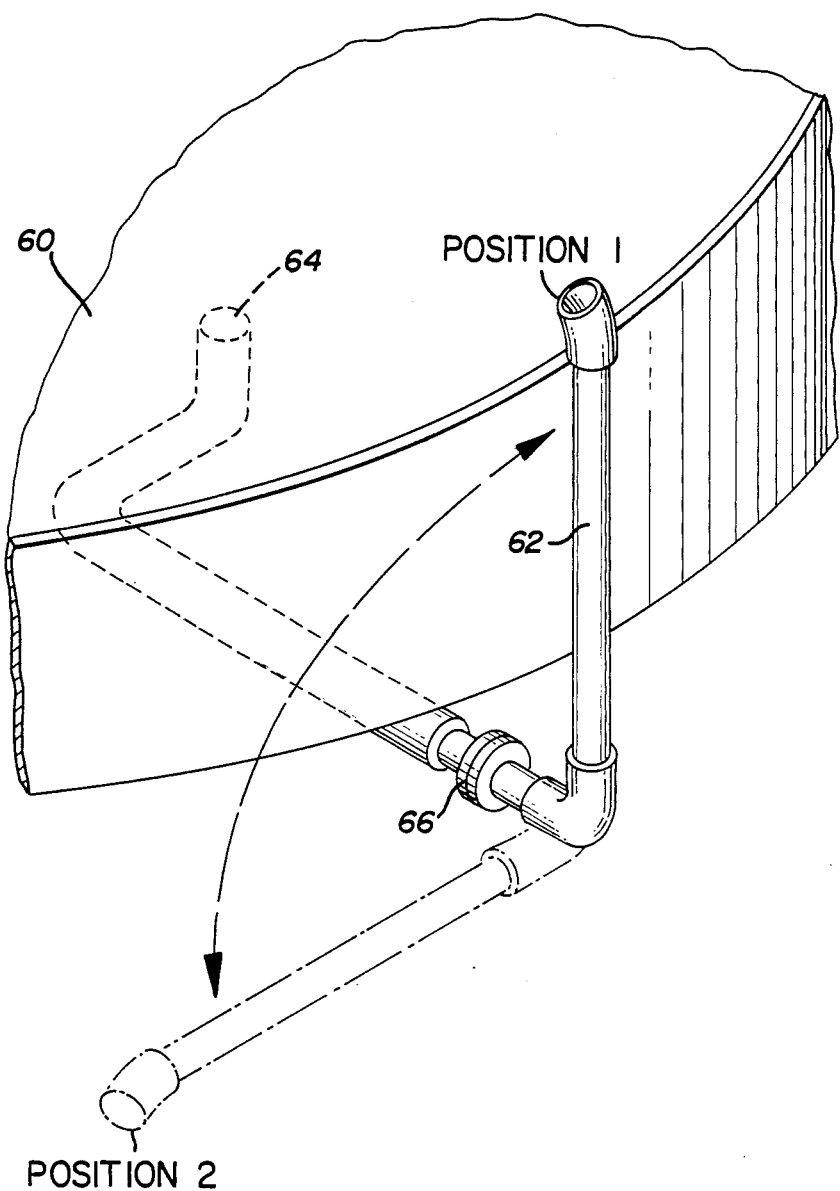

DROPLET FREEZING METHOD AND APPARATUS

BACKGROUND OF THE INVENTION

1. Field of the Invention

This invention relates to a method and apparatus for producing free flowing particles comprised of frozen droplets made from a solution of a biological or organic material.

2. Background Art

Biological or organic materials, such as those occurring in food products and drugs, are frequently not a solid at room temperature, or exhibit characteristics which cause them not to be free flowing. These materials are often difficult to handle or process and are not readily measured and separated into small quantities. Being organic in nature, these materials tend to spoil or degrade on storage, reducing their useful lifetime and creating quality control problems.

One method of altering the physical characteristics of such materials to make them more free flowing, while simultaneously increasing their shelf life or useful storage period is to freeze them. Often times the material to be frozen is a solution of the biological or organic material. This is particularly true when it is desired to control the concentration of such material closely. It is also helpful to place the biological or organic material into solution when its non diluted form is difficult to handle. By placing the material into solution and then freezing droplets of the material, it is possible to produce free-flowing particles of the desired concentration of organic material. The particles can be stored for long periods of time in a frozen condition with little change in freshness or active strength.

Freezing of liquids into droplets has been accomplished previously; however, the methods used have not been adequate for large scale, rapid, continuous production of consistent product of the type desired for the application which led to development of the method and apparatus described herein.

U.S. Pat. No. 4,712,310 to Roy describes a technique for co spray preparation of homogeneous hybrid powders suitable for preparing tablets. The tablets are useful as reagent carriers for diagnostic assays. Two separate solutions are prepared and simultaneously sprayed from hypodermic needles onto the surface of a moving bath of boiling fluorocarbon refrigerant. The solutions are sprayed through separate spray needles in a manner to form hybrid droplets which are immediately frozen. The frozen droplets are collected and lyophilized.

U S. Pat. No. 4,687,672 to Vitrovsky describes the preparation of free flowing food particles. Particles of solid food, or extruded viscous food, or food in a liquid form pumped through apertures is frozen in a bath of cryogenic liquid, and then fractured into particles which are screened to remove fines. Such fractured particles are somewhat irregular in shape and not as free flowing as desired for applications such as those for which the present invention is intended. The process of the present invention does not require a fracturing step and thus provides a more uniformly shaped particle.

U.S. Pat. No. 4,655,047 to Temple et al. discloses chilling or freezing of liquid food substances, in particular liquid egg. The substance to be frozen, in liquid form, is allowed to fall a short drop height onto the surface of liquid nitrogen. The substance may fall from a tube as a continuous stream or may drip from the tube onto the liquid nitrogen surface. The patent also discloses that the technique might be used for freezing liquid soap and liquids containing bacteria cultures.

U S. Pat. No. 4,077,227 to Larson discloses a method of freezing a liquid material such a blood and semen using a technique which inhibits agglomeration of droplets of the material during freezing. The liquid is first separated into successive drops, each of which is subjected to an electric field to induce an electric charge of the same polarity on each drop. The electronic charge on the drops keeps them apart so they freeze as individual droplets.

U.S. Pat. No. 3,932,943 to Briggs et al. describes a process for preparation of a particulate product of a substance containing at least one biologically active component. The substance is placed in a solution or colloidal suspension and is sprayed above a moving bath of fluorocarbon refrigerant. The spraying is conducted from a sufficient height above the refrigerant that the spray can form into droplets of solution prior to contact with the fluorocarbon refrigerant whereby the droplets are frozen. The frozen droplets are subjected to a vacuum at a temperature such that essentially all of the liquid in the droplets sublimes, forming particles from the frozen droplets. Use of fluorocarbon refrigerant is considered critical so the frozen droplets will float on the refrigerant and so the desired heat transfer rate can be achieved. The typical particle size of the frozen droplets is estimated to be in the range of about 180 microns (0.18 mm), since they were collected on an 80 mesh sieve.

U.S. Pat. No. 3,755,530 to Avila et al. describes a method of treatment of waste solutions, wherein a liquid solution of solid wastes in injected into a refrigerant liquid through an orifice disposed at the bottom of a vessel containing the refrigerant liquid. Water is subsequently removed from the frozen solution by the sublimation of ice in a controlled vacuum.

U.S. Pat. No. 3,721,725 to Briggs et al. discloses a method of making a homogeneous solid particulate blend of solid initial ingredients. The method involves spraying a solution of the solid ingredients into boiling dichlorodifluoromethane or other fluorocarbon refrigerant and lyophilizing the resulting frozen droplets.

U.S. Pat. No. 3,551,533 to Monforte et al. discloses a method of freeze drying an atomized liquid solution, e.g. a solution of refractory type materials. The method requires subsequent removal of the solvent used by sublimation from the frozen droplets to leave a product in the form of a uniform fine powder.

Many of the above methods utilize an atomized spray of the liquid to be frozen, which results in the formation of very fine particles, typically in the size range of 50 to 500 microns (275 to 35 mesh USA Standard) and having a broad distribution of particle sizes. Other methods disclose formation of individual globules or droplets and their disposition onto the surface of a cryogenic liquid. Formation of individual droplets which are allowed to drip or which are extruded one by one is a relatively slow process. In one of the methods, for freezing of liquid food substances, a continuous stream of the liquid flows under pressure from a tube into liquid nitrogen and breaks up into droplets upon contact with the nitrogen surface. Droplets formed in this manner generally are not uniform in size.

Once the droplets or globules of material are formed and frozen within the cooling liquid, it is necessary to recover them from the cooling liquid. Most of the above described patents disclose that the frozen globules are more dense than the cooling liquid, and thus the frozen globules settle to the bottom of the tank holding the cooling liquid. The frozen droplets or globules are then transported by a conveyor means out of the tank containing the cooling liquid. In two of the cases, the frozen droplets or globules are said to be less dense than the freezing refrigerant and to float in the freezing refrigerant. In one of these cases, a liquid food substance is discharged from a nozzle into a trough of cryogenic liquid and the material in the trough is passed through a screen to remove the frozen product prior to recirculation of the cryogenic liquid back to the beginning of the trough. However, this latter method does not deal with the possibility of agglomeration of freezing globules or droplets, since the only motion at the surface of the cryogenic liquid is the flow of the cryogenic liquid along the trough toward the screen. In the other case, the refrigerant liquid is removed from the frozen droplets by sublimation, under a vacuum.

Thus, it would be useful to have a method of forming essentially spherical frozen droplets of uniform size and uniform droplet composition which are comprised of biological or organic material, wherein the method permits droplet formation at a rapid rate while still permitting formation of larger sized individual droplets than can be obtained by atomizing techniques. In addition, it would be useful to have an improved method of removing the frozen droplets from a cryogenic liquid used to freeze them, particularly when the frozen droplets are less dense than the cryogenic liquid and tend to float toward the liquid surface where particle agglomeration with unfrozen liquid droplets can take place.

SUMMARY OF THE INVENTION

In accordance with the present invention, a method and apparatus are disclosed which enable the generation of essentially spherical frozen droplets from a liquid biological or organic-comprising composition.

The method comprises the following steps:

(a) feeding a first liquid comprising a biological or organic material at a positive pressure through a nozzle or through an orifice in a manner which provides a continuous stream of the first liquid exiting from the nozzle or orifice;

(b) causing the stream of first liquid to travel through a fluid comprising a gas or vapor for a distance sufficient to cause the stream to break apart, so that droplets of the first liquid are formed in the gas-comprising fluid, wherein the droplets range in average diameter from about 0.6 mm to about 5 mm;

(c) contacting the droplets with a cryogenic second liquid capable of freezing the droplets into a solid phase at the temperature of the cryogenic second liquid;

(d) concentrating the frozen droplets of step (c) in a portion of the volume of the cryogenic second liquid; and, (e) separating the frozen droplets from the cryogenic second liquid by removing them from the volumetric portion of the cryogenic second liquid in which they have been concentrated.

When the frozen droplets tend to have a relatively rapid settling rate in the cryogenic second liquid, gravity can be used to concentrate the frozen droplets into one portion of the cryogenic second liquid. When the frozen droplets have a tendency to float in the cryogenic second liquid, the following technique has been discovered to work particularly well. As the droplets of the first liquid comprising a biological or organic material are continually fed into the cryogenic second liquid in the cryogenic bath, the mixture of frozen droplets and cryogenic second liquid is continually agitated to provide contact with a deflector plate having openings therein which permit the cryogenic second liquid to pass through the plate while deflecting the frozen droplets. The frozen droplets are deflected so that they collect (concentrate) in the desired portion of the volume of the cryogenic second liquid. The frozen droplets are then continually separated from the volumetric portion of the cryogenic bath into which they have been collected.

The frozen droplets formed by the method of the present invention are essentially spherical and have an average diameter ranging from about 0.6 mm to about 5 mm. The preferred average diameter of the frozen droplets is about 1.5 mm. Typically the frozen droplets are substantially uniform in cross-sectional composition.

An apparatus for forming frozen droplets by the above method comprises:

(a) a pressurized liquid feed means capable of providing at least one continuous stream of a first liquid comprising a biological or organic material exiting from the feed means;

(b) means for contacting the at least one continuous stream with a fluid comprising a gas or vapor for a time period sufficient to cause the stream to break apart, forming droplets of the first liquid within the gas or vapor, said gas or vapor contacting means in communication with said liquid feed means;

(c) means for contacting the droplets with a cryogenic second liquid in a manner which causes the droplets to freeze into a solid phase, and wherein the frozen droplets have an average diameter ranging from about 0.6 mm to about 5 mm, said cryogenic second liquid contacting means in communication with said gas or vapor contacting means.

The apparatus can also include the following elements:

(d) means for concentrating the frozen droplets within a portion of the contacting cryogenic second liquid;

(e) means for removing the frozen droplets from the concentration of frozen droplets within the portion of the cryogenic second liquid;

(f) means for substantially separating residues of the cryogenic second liquid from the frozen droplets after their removal from the portion of the cryogenic second liquid in which they were concentrated;

(g) means for returning the residues of the cryogenic second liquid separated from the frozen droplets in step (f) to the contacting means of step (c).

DEFINITIONS

Frozen droplets as used in the specification and claims herein means essentially spherical particles having at least a crust of solid material at the outer surface of the spherical particle. The spherical particle can be comprised of solid material entirely.

Cryogenic liquid as used in the specification and claims herein means a liquefied gas having a normal boiling point below about −75° C., preferably below −150° C. (−240° F.).

A continuous stream as used in the specification and claims herein means a contiguous thin column of liquid.

A pressurized nozzle or pressurized orifice as used in the specification and claims herein means a conduit containing fluid under pressure and having an opening through which the fluid exits under pressure.

Deflector plate as used in the specification and claims herein means a substantially smooth surface having openings therein which is used to direct frozen droplets to a desired concentration or collection volume in a cryogenic bath.

Uniform droplet compositions as used in the specification and claims herein means essentially consistent droplet composition from droplet to droplet.

BRIEF DESCRIPTION OF THE DRAWINGS

FIG. 2 shows the details of a swing pipe assembly which can be used in combination with a freeze tank for carrying out the method of the present invention. The swing pipe is used to recover frozen droplets that tend to settle to the bottom of the freeze tank.

DETAILED DESCRIPTION OF THE INVENTION

Figure 1:
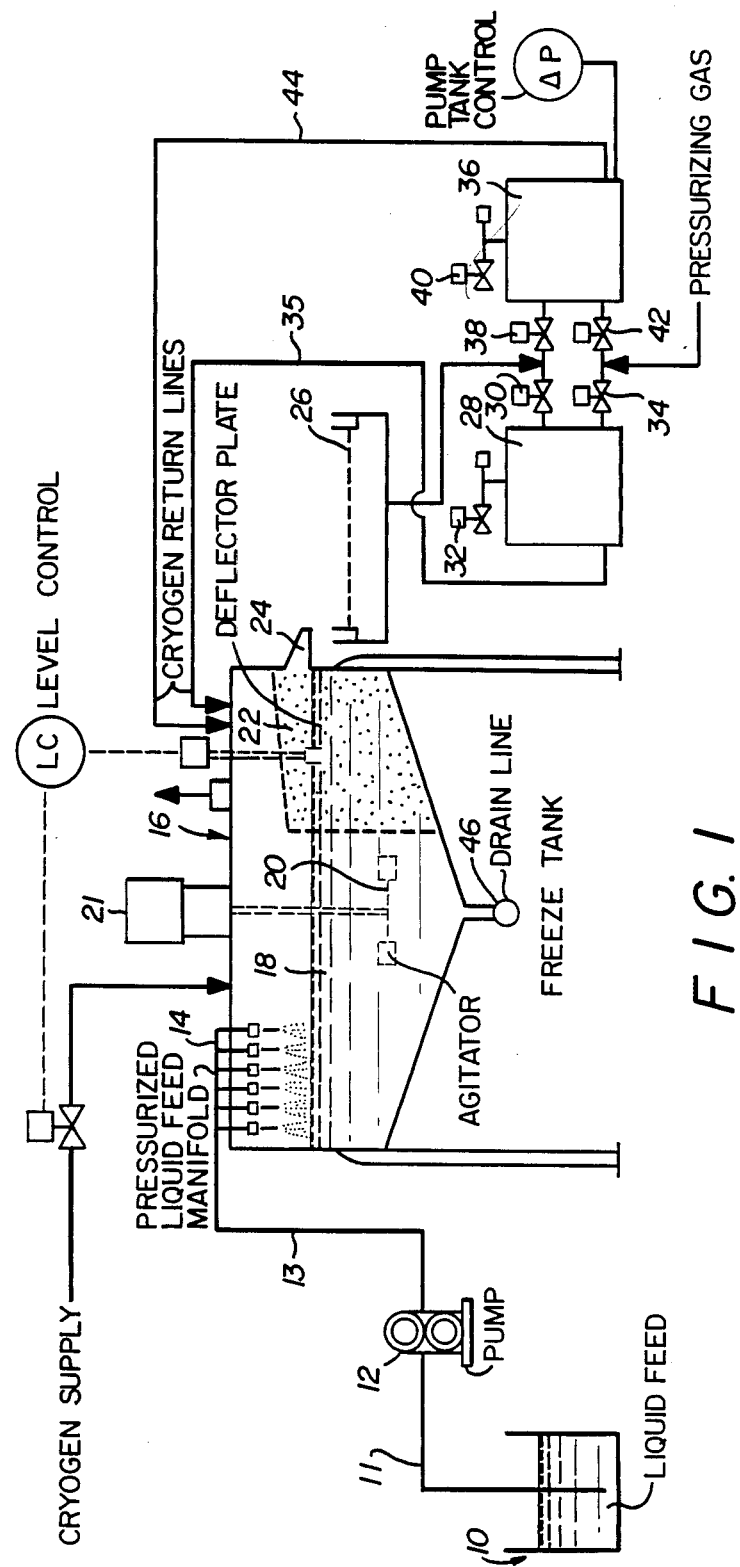
FIG 1 shows one embodiment of the droplet freezing apparatus; this embodiment is designed for removal of frozen droplets which tend to float in the cryogenic liquid.

In accordance with the present invention, a method and apparatus are disclosed which enable the generation of essentially spherical, substantially uniform droplet composition, frozen droplets from liquids comprised of biological or organic materials. Frozen droplets formed by the method of the present invention typically range in size from about 0.6 to about 5 mm in diameter. The method enables production of frozen droplets in a continuous and uniform manner at a relatively high production rate. The method is generally not subject to tube or capillary clogging of feed means used to feed the liquid biological or organic material into the liquid cryogen which is used to freeze the droplets.

Typically the biological or organic liquid is in the form of a solution. The liquid is pumped under pressure through at least one nozzle or orifice which produces a stream of liquid from the end of the nozzle. To increase the droplet production rate, a number of nozzles or orifices are arranged in an advantageous position relative to each other and are positioned in the vapor space above a bath containing a cryogenic liquid. The distance between the tips of the nozzles or orifices and the cryogenic bath surface must be sufficient that the stream of liquid exiting the nozzle breaks up into droplets in the gas or vapor space above the liquid cryogenic bath, prior to contacting the surface of the cryogenic liquid. The droplet size can be varied within certain limits. The droplet size depends on parameters such as the nozzle or orifice design (especially the opening diameter). the pressure applied to the liquid to force the liquid out of the nozzle, and characteristics of the liquid itself, such as liquid viscosity at the temperature and pressure at which the liquid exits the nozzle, and liquid surface tension. If too much pressure is applied, the liquid can exit the nozzle as a spray rather than as a uniform stream, and this can result in a wider distribution of droplet size diameters, particularly including undesired numbers of fine sized droplets. Thus, for a given liquid, there are optimum temperature and pressure conditions as well as a design range of nozzle or orifice opening diameters which will provide the substantially uniform particle size frozen droplets desired.

Optimum operating conditions are readily established by one skilled in the art after equipment design has been finalized.

The inside diameter of the nozzle or orifice from which the organic or biological liquid feed is to exit can vary from about 0.1 mm to about 1 mm, preferably from about 0.15 to about 0.7 mm, and most preferably from about 0.25 to about 0.5 mm, with the specific size employed in a particular operation influenced by the composition of the liquid feed and the operating pressure and temperature.

The pressure at which the liquid feed is to be pumped through the nozzle or orifice can vary from about 10 psig to about 100 psig, but is preferably less than about 90 psig, given the nozzle or orifice inside diameter range described above. The pressure to be applied will depend on the physical characteristics of the liquid feed under operating conditions. The maximum pressure to be applied must be such that a spray is not created, since once the stream of liquid exiting the nozzle or orifice begins to form a spray, fine particles below the desired minimum diameter of about 0.6 mm are formed.

The viscosity of the liquid feed at the temperature and pressure of operating conditions can vary over a wide range and is not considered to be critical. However, the liquid feed should have a viscosity that permits ready flow through the nozzle or orifice at a reasonable pressure. Typically the viscosity can range from about 1 to about 20,000 centipoise at operating conditions.

The nozzles are spaced in a manner which generally prevents droplets from contacting each other prior to contacting the cryogenic liquid. The location of the nozzles within a tank which contains a cryogenic liquid is in the vapor space above the cryogenic liquid. The nozzles must be spaced a sufficient distance above the cryogenic liquid surface to permit the stream of organic or biological liquid to break up into droplets prior to contacting the cryogenic liquid. However, spacing the nozzles too great a distance above the cryogenic liquid permits liquid feed droplets to drift within the vapor space above the cryogenic liquid, whereby they can contact each other and agglomerate. Spacing the nozzles an excessive distance above the cryogenic liquid can also result in deformation of the liquid feed droplets as they travel through the vapor space prior to contacting the cryogenic liquid, whereby the frozen droplets formed are not substantially uniform and spherical in shape. It is also important that the nozzles be spaced a sufficient distance above the liquid cryogen surface that the cryogenic liquid does not splash onto the tip of the nozzle, freezing the liquid feed and plugging the nozzle exit opening. Thus, for a given cryogenic bath and agitation design, combined with a specific nozzle design and arrangement, there is a preferred spacing range between the nozzle tips and the cryogenic liquid bath for a given liquid feed. The preferred spacing between nozzle tips and cryogenic liquid surface can be determined by minimal experimentation once other design variables are specified. The nozzles are spaced relative to each other in a manner which enables liquid feed droplets to contact the cryogenic liquid and form at least a frozen crust on the droplet surface prior to contacting other droplets which are also in the process of freezing, thus preventing agglomeration. Since agitation of cryogenic liquid within the cryogenic bath also affects whether droplets form a frozen surface crust prior to contacting other freezing droplets, the agitation design of the liquid cryogen bath and the location of the nozzles are interdependent.

Once the organic or biologically comprised liquid feed enters the cryogenic liquid bath, it freezes very rapidly, given a substantial temperature difference exists between the cryogenic liquid bath and the liquid feed, a droplet size in the range previously discussed, and good agitation of the cryogenic liquid bath. It is necessary to remove the frozen droplets continually and rapidly to prevent agglomeration of frozen droplets which contact unfrozen liquid feed droplets on the liquid cryogen bath surface. An agitator, such as a flat bladed turbine, submerged in the liquid cryogen bath can be used to provide a swirling flow of the cryogenic liquid which quickly moves the frozen droplets out of the droplet producing area. Use of a circular, conical-bottomed tank as the vessel containing the liquid cryogen bath assists in creating the desired swirling flow pattern. The cryogenic liquid bath level is maintained by an automatic level control means selected from those known in the art.

The cryogenic liquid bath is agitated to cause a swirling motion of the bath in the freeze tank and in a manner that the surface movement of the bath is essentially free of splash. This swirling motion serves to move the entering feed liquid droplets away from the point at which they enter the cryogenic liquid bath, thus preventing agglomeration. At the same time, the frozen feed composition droplets are carried to the freeze tank location at which the frozen droplets are collected and removed from the freeze tank. This permits continuous operation of the process at high production rates. The rate of agitation will vary over a wide range and will depend on the agitator and tank design and sizing. The agitation rate should be such that the frozen droplets are not damaged to any significant extent by the agitation.

When the density and surface chemistry characteristics of the frozen droplets are such that the frozen droplets tend to settle at a sufficiently rapid rate in the cryogenic liquid, the frozen droplets can be collected in the bottom of the bath tank by gravity and removed therefrom.

One method of continually removing the frozen droplets from the bottom of the cryogenic bath tank (freeze tank) is to periodically drain the contents of the bottom portion of the tank. Experience has shown that valves typically available within the industry tend to plug as the frozen droplets collect in the bottom of the freeze tank and piping therefrom. The problem was solved by developing a swing pipe. The swing pipe, one embodiment of which is shown in FIG. 2, depends on the static head of liquid in the pipe 62 in its vertical position to prevent the frozen droplet-cryogenic liquid mixture in the bottom of the freeze tank 60 from flowing out of opening 64 in the bottom of the tank 60. Swing pipe 62 is attached to piping connected with opening 64 by means of a rotary joint 66. When swing pipe 62 is in a fully vertical position, Position 1, the frozen droplet-cryogenic liquid mixture does not flow from freeze tank 60. When swing pipe 62 is in a fully horizontal position, Position 2, the frozen droplet-cryogenic liquid mixture flows freely from the bottom of freeze tank 60. By positioning swing pipe 62 between Position 1 and Position 2, it is possible to control the rate at which the frozen droplet- cryogenic liquid mixture flows out of freeze tank 60. Use of the swing pipe eliminated pipeline and valve plugging problems previously observed when valves of the kind known in the art were used to control the flow of the frozen droplet-cryogenic liquid mixture from the bottom of freeze tank 60. Cryogenic liquid flowing out of freeze tank 60 with the frozen droplets can be separated from the droplets using techniques known in the art and can be recycled back into freeze tank 60.

When the density and the surface chemistry of the frozen droplets is such that the frozen droplets tend to float in the cryogenic liquid, a particularly useful method of removing the frozen droplets is to locate a deflector plate having openings therein, such as a perforated plate, in the cryogenic liquid bath. The deflector plate is located in a manner which directs the frozen droplets to one volumetric area of the bath (preferably away from the liquid solution feed means) where the frozen droplets are allowed to flow over a discharge weir along with some of the cryogenic liquid. Frozen droplets which have flowed over the weir along with cryogenic liquid are separated from the cryogenic liquid using a screen (which may be vibrated) from which the frozen droplets are continually or periodically collected, and the cryogenic liquid is permitted to flow through the screen into one or more "pump" tanks. The pump tanks can be periodically pressurized to transfer the cryogenic liquid back into the bath. It is preferred to have openings in the deflector plate which are in the size range of the average diameter frozen droplet formed. It is desired to have the largest amount of opening area of the deflector plate surface as possible, since this reduces the pressure drop across the plate and prevents the back up of cryogenic liquid in front of the plate, formation of eddi currents and other fluid flow problems. The size of the plate openings must be such that substantially all of the frozen droplet particles contacting the plate do not pass through the plate. Most often the frozen droplets do not contact the plate in a head on direction, so the average diameter frozen droplets collected by the plate can be smaller than the average diameter of openings in the plate. The plate openings should be of constant dimension all the way through the plate, to avoid frozen droplets becoming caught inside the opening or being deformed or fractured by the plate. The openings typically are circular in shape for ease in fabrication of the plate. However, other shaped openings which would not tend to plug with frozen droplets or to deform the frozen droplets can be used. Typically the percentage of plate which is opening space is at least about 20%. Deflector plates having 40% to 50% of the plate surface as opening space have performed well in the apparatus of the present invention.

The deflector plate surface can be flat or curved. The deflector plate is installed in the freeze tank in a manner such that it can be interchanged with other deflector plates having other opening dimensions or can be removed, depending on the liquid feed to be processed.

The purpose of the deflector plate is to deflect and direct the frozen droplets in the swirling cryogenic liquid bath toward the discharge weir while permitting the cryogenic liquid to pass through the deflector plate. By permitting the cryogenic liquid to pass through the deflector plate, the flow of cryogenic liquid within the bath is less disturbed by the presence of the deflector plate, and the pressure against the deflector plate is reduced, thus reducing the probability that frozen droplets will be deformed from the desired spherical shape by being pressured against the deflector plate.

EXAMPLE 1

A schematic of one of the preferred apparatus embodiments of the present invention is shown in FIG. 1. This apparatus was used to freeze droplets of a liquid feed composition comprised of about 20 weight percent powdered milk and about 80 weight percent water. The powdered milk solution was fed from a feed solution tank 10 through a solution pump 12, which applied sufficient pressure to the milk solution to force it through solution feed manifold 14 into freeze tank 16. The temperature of the milk solution was about 5° C. The solution pump 12 was a variable speed positive displacement gear pump, although many other kinds of positive displacement pumps are known and can be used. The operating discharge pressure of solution pump 12 ranged from about 10 psig to about 100 psig during experimentation, with a preferred pressure of about 60 psig for processing the milk solution described above. The viscosity of the milk solution was about 33 centipoise at this temperature and pressure. The solution feed manifold 14 was comprised of an arrangement of hypodermic needles or small diameter tubings. During experimentation, the needle or tubing openings ranged in diameter from about 0.15 mm to about 0.7 mm. The preferred diameter opening for the needle or tubing was about 0.4 mm to produce frozen droplets averaging about 2 mm in diameter when the solution to be frozen had a viscosity of about 30 to 35 centipoise at about 5° C. Hypodermic needles were used as a convenient tubing for this application, due to their availability at relatively low cost. The needles were arranged about 25 to about 50 mm apart radially from the center of the freeze tank 16 toward the outside wall of the tank. The tips of the needles were positioned about 200 to about 400 mm above the surface of cryogenic liquid 18 in freeze tank 16. The liquid cryogen 18 was liquid nitrogen at a temperature of about $-198.5°$ C. The freeze tank 16 was comprised of an insulated stainless steel tank about 1.83 meters in diameter, containing an approximately 30 cm depth of liquid nitrogen 18, to provide the cryogenic bath. The bottom of freeze tank 16 was a conical shape having an incline of about 18° from horizontal. A flat bladed turbine 20 about 46 cm in diameter driven by a variable speed ¾ HP motor 21 at about 80 to about 200 RPM was used to circulate liquid nitrogen 18 in tank 16. A perforated deflector plate 22 having about 1.6 mm diameter holes therein was used to direct the frozen particles to overflow weir 24 from which the frozen particles moved onto product separation screen 26. In our laboratory equipment, the frozen droplets were removed batch-wise from product separation screen 26; however, there are numerous systems known in the art, such as vibrating screens and conveyors which could be used for continuous collection of the frozen droplets. The frozen droplets produced ranged in size from about 0.6 to about 3 mm in diameter, with an average particle diameter of about 2 mm.

The small quantity of liquid nitrogen which overflows through weir 24 along with the frozen droplets, flows through product separation screen 26 and into one or more pump tanks. The drawing shows two pump tanks, 28 and 36. Use of two pump tanks permits filling of one pump tank with liquid nitrogen flowing from product separation screen 26 while the second pump tank is under pressure, enabling return of recycled liquid nitrogen from the second pump tank to freeze tank 16. For example, when pump tank 28 is full, a liquid level switch (not shown on the drawing) closes inlet valve 30 and vent valve 32 on tank 28, and opens a nitrogen pressurizing valve 34, pressure transferring the liquid nitrogen back into freeze tank 16 through transfer line 35. While pump tank 28 is transferring liquid nitrogen to freeze tank 16, pump tank 36 has inlet valve 38 and vent valve 40 open and nitrogen pressuring valve 42 closed, so that liquid nitrogen from product separation screen 26 can enter pump tank 36. The typical pressure on a pump tank 28 or 36 during pressuring of liquid nitrogen from the tank back to freeze tank 16 is about 10 psig.

The present method permits formation of solid single frozen particles as distinguished from methods which provide a particle which is an agglomeration of smaller particles. Agglomerated particles can break apart on handling to produce undesired fine particles (fines). The cross-sectional composition of frozen droplets formed by the present method is uniform, providing the possibility of controlled dissolution phenomena. The overall composition of frozen droplets formed by the method of the present invention is uniform from droplet to droplet as distinguished from agglomerated particles which can vary in composition from agglomerated particle to agglomerated particle.

EXAMPLE 2

A smaller scale apparatus similar to the apparatus described in EXAMPLE 1, and the process described in EXAMPLE 1 were used to process a CELLOSIZE ® Hydroxyethyl Cellulose solution in water. CELLOSIZE is a registered trademark of Union Carbide Corporation. The CELLOSIZE comprised about 0.3 weight percent of the solution which exhibited a viscosity of about 130 centipoise at a temperature of about 20° C. The solution was fed from feed tank 10 through feed pump 12 which provided a pressure of about 60 psig in feed line 13 to feed manifold 14. The inside diameter of the hypodermic needles comprising feed manifold 14 was about 0.24 mm. The spacing between the needle tips and the surface cryogenic liquid (nitrogen) 18 in tank 16 was about 350 mm. The frozen droplets produced were essentially spherical in shape, having diameters substantially ranging from about 2 mm to about 4 mm. Under the above conditions, at least 76 weight percent of the droplets exhibited a diameter larger than about 2 mm.

EXAMPLE 3

The general apparatus and process described in EXAMPLE 2 were used to process a CELLOSIZE Hydroxyethyl Cellulose solution comprising about 0.75 weight percent CELLOSIZE in water. The viscosity of the solution was about 4,450 centipoise at about 20° C. The solution was fed from feed tank 10 through feed pump 12 which provided a pressure of about 60 psig in feed line 13 to manifold 14. The inside diameter of the hypodermic needles comprising feed manifold 14 was about 0.24 mm. The spacing between the needle tips and the surface of cryogenic liquid (nitrogen) 18 in tank 16 was about 380 mm. The frozen droplets produced were essentially spherical in shape, having diameters substantially ranging from abut 2 mm to 5 mm. Under the above conditions, at least 88 weight percent of the droplets exhibited a diameter larger than about 2 mm.

EXAMPLE 4

The general apparatus and process described in EXAMPLE 2 was used to process a biological culture supplied by a research laboratory for experimental purposes. The viscosity of the culture was about 19 centipoise at about 13° C. The culture was fed from a liquid feed tank through a feed pump which provided a pressure of about 60 psig in a feed line leading to a single hypodermic needle. The inside diameter of the hypodermic needle was about 0.32 mm. The spacing between the needle tip and the surface of cryogenic liquid (nitrogen) 18 in tank 16 was about 380 mm. The frozen droplets produced were essentially spherical in shape, having diameters ranging from about 2 mm to about 4 mm. Under the above conditions, at least 78 weight percent of the droplets exhibited a diameter larger than about 2 mm.

The above examples illustrate typical preferred embodiments for application of the present invention and the best mode of the invention as presently contemplated. However, this invention has a broad range of applicability and is susceptible to modification and alternate constructions based on the embodiments disclosed. Consequently, it is not intended that the above-described embodiments act as limitations of this invention. On the contrary, the intent is to include all modifications and alternate constructions falling within the spirit and scope of the invention as expressed in the appended claims.

What is claimed is:

1. A method of forming essentially spherical frozen droplets from a liquid composition comprising a biological or organic material, comprising the steps of:

(a) feeding a first liquid comprising a biological or organic material at a positive pressure through a nozzle or through an orifice in a manner which provides a continuous stream of said first liquid exiting from said nozzle or orifice;

(b) causing said stream of first liquid to travel through a fluid comprising a gas or vapor for a distance sufficient to cause said stream to break apart, forming liquid droplets ranging in average diameter from about 0.6 mm to about 5 mm;

(c) contacting said droplets with a cryogenic second liquid contained in a vessel, wherein said cryogenic second liquid is agitated in a manner which creates motion at the point of contact between said droplets and said cryogenic second liquid, whereby agglomeration of said droplets prior to freezing of said droplets is essentially prevented;

(d) concentrating said frozen droplets in a portion of the volume of said cryogenic second liquid by permitting gravity to pull said frozen droplets from a first portion of the volume of said cryogenic second liquid toward a second portion of the volume of said cryogenic second liquid; and (e) separating said frozen droplets from said second portion of the volume of said cryogenic second liquid.

2. A method of forming essentially spherical frozen droplets from a liquid composition comprising a biological or organic material, comprising the steps of:

(a) feeding a first liquid comprising a biological or organic material at a positive pressure through a nozzle or through an orifice in a manner which provides a continuous stream of said first liquid exiting from said nozzle or orifice;

(b) causing said stream of first liquid to travel through a fluid comprising a gas vapor for a distance sufficient to cause said stream to break apart, forming liquid droplets ranging in diameter from about 0.6 mm to about 5 mm;

(c) contacting said droplets with a cryogenic second liquid contained in a vessel, wherein said cryogenic second liquid is agitated in a manner which creates motion at the point of contact between said droplets and said second cryogenic liquid whereby agglomeration of said droplets prior to freezing of said droplets is essentially prevented;

(d) concentrating said frozen droplets in a portion of the volume of said cryogenic second liquid by contacting an agitated mixture of said frozen droplets and said cryogenic second liquid with a deflector plate having openings therein, said plate permitting at least the major portion of said cryogenic second liquid to pass through said deflector plate while deflecting said frozen droplets in a manner which causes said frozen droplets to collect in said concentrating portion of said volume of said cryogenic second liquid; and, (e) separating said frozen droplets from said concentrating portion of said volume of said cryogenic second liquid.

3. The method of claim 2, wherein said deflector plate having openings therein comprises a plate having essentially circular-shaped openings through said plate, said openings having diameters which are at least about equal to the average diameter of the frozen droplets formed.

4. The method of claim 3 wherein said openings comprise at least about 20% of the surface of said plate.

5. The method of claim 1 or claim 2, wherein said frozen droplets which are essentially spherical have an average diameter ranging from about 0.6 mm to about 5 mm.

6. The method of claim 5 wherein said frozen droplets have a diameter size distribution such that at least 75 weight percent of the frozen droplets have a diameter larger than about 2 mm.

7. The method of claim 5 wherein the composition of said frozen droplets is substantially uniform from droplet to droplet.

8. An apparatus for forming frozen droplets, said apparatus comprising:

(a) a pressurized liquid feed means capable of providing at least one continuous stream of a first liquid composition comprising a biological or organic material from said feed means;

(b) means for contacting said at least one continuous stream with a fluid comprising a gas or a vapor for a time period sufficient to cause said stream to break apart and form droplets of said first liquid within said gas or vapor, said gas or vapor contacting means in communication with said liquid feed means;

(c) means for contacting said droplets with a cryogenic second liquid in a manner which causes said droplets to freeze into a solid phase, whereby frozen droplets having an average diameter ranging from about 0.6 mm to about 5 mm are formed, said cryogenic second liquid contacting means in communication with said gas or vapor contacting means;

(d) means for concentrating said frozen droplets with a concentrating portion of said cryogenic second liquid;

(e) means for removing said frozen droplets from said concentration of frozen droplets in said concentrating portion of said cryogenic second liquid; and, (f) means for substantially separating residues of said cryogenic second liquid from said frozen droplets after removal of said frozen droplets from said concentrating portion of said cryogenic second liquid.

9. The apparatus of claim 8, including an additional element:

(g) means for returning said residues of cryogenic second liquid separated from said frozen droplets in step (f) to said contacting means of step (c).

10. The apparatus of claim 9, wherein said liquid feed means comprises at least one nozzle or orifice having an inside diameter ranging between about 0.1 mm and about 1 mm.

11. The apparatus of claim 10 wherein said means for contacting said droplets with said cryogenic second liquid comprises a vessel containing said cryogenic second liquid and containing a gas or vapor space in the upper portion of said vessel above said cryogenic second liquid, wherein said gas or vapor space is in communication with said pressurized liquid feed means and wherein said cryogenic second liquid is agitated in a manner which creates a swirling motion at the surface of said cryogenic second liquid as it contacts the droplets of said first liquid, whereby agglomeration of said droplets prior to freezing or during freezing is reduced or substantially eliminated.

12. The apparatus of claim 11, including a means for concentrating frozen droplets within a concentrating portion of said cryogenic second liquid in said vessel, wherein said concentrating means uses gravitational forces to move said droplets from other portions of said second liquid toward said concentrating portion of said cryogenic second liquid.

13. The apparatus of claim 12, wherein said means for removing said frozen droplets from said concentrating portion of said contacting liquid comprises a swing pipe assembly.

14. The apparatus of claim 11 wherein said means for concentrating said frozen droplets within a concentrating portion of said cryogenic second liquid comprises a deflector plate having openings therein, said plate being disposed within said cryogenic second liquid in a manner which permits said second cryogenic liquid to pass through said openings in said plate while directing said frozen droplets toward said concentrating portion of said cryogenic second liquid.

15. The apparatus of claim 14, wherein said openings in said plate are essentially circular-shaped openings through said plate, said openings having diameters which are at least about equal to the average diameter of said frozen droplets.

16. The apparatus of claim 14 wherein said openings comprise at least 20% of said plate surface.

17. The apparatus of claim 14 wherein said means for removing said frozen droplets from said concentration of frozen droplets comprises an exit weir placed at about cryogenic liquid level in said vessel containing said cryogenic second liquid and wherein said concentrating portion of said second liquid is in the area of said weir, whereby said frozen droplets are caused to flow out of said vessel through said weir.

18. The apparatus of claim 17, wherein said means for substantially separating said cryogenic second liquid from said frozen droplets after removal of said frozen droplets from said concentration of frozen droplets comprises a surface having openings therein, such as a screen, and wherein said cryogenic second liquid passes through said openings while said frozen droplets do not pass through, but collect on said surface.

* * * * *

UNITED STATES PATENT AND TRADEMARK OFFICE
CERTIFICATE OF CORRECTION

PATENT NO. : 4,848,094
DATED : July 18, 1989
INVENTOR(S) : R.B. Davis et al

It is certified that error appears in the above-identified patent and that said Letters Patent is hereby corrected as shown below:

In claim 2, line 10 between "gas" and "vapor" insert --or--.

Signed and Sealed this

Fifth Day of June, 1990

Attest:

HARRY F. MANBECK, JR.

*Attesting Officer*      *Commissioner of Patents and Trademarks*